United States Patent [19]

Dutra

[11] 4,323,387

[45] Apr. 6, 1982

[54] N-THIOLCARBONYL DERIVATIVES OF N-PHOSPHONOMETHYLGLYCINONITRILE ESTERS, HERBICIDAL COMPOSITIONS AND USE THEREOF

[75] Inventor: Gerard A. Dutra, Ladue, Mo.

[73] Assignee: Monsanto Company, St. Louis, Mo.

[21] Appl. No.: 172,883

[22] Filed: Jul. 28, 1980

[51] Int. Cl.$^3$ .................... C07C 155/02; A01N 57/18
[52] U.S. Cl. ..................................... 71/87; 260/455 P
[58] Field of Search ......................... 260/455 P; 71/87

[56] References Cited

U.S. PATENT DOCUMENTS 3,991,095 11/1976 Gaertner ................................. 71/87
4,067,719 1/1978 Dutra ..................................... 71/87

OTHER PUBLICATIONS

Wagner et al., "Synthetic Organic Chemistry," J. Wiley & Sons Inc., (1953) pp. 412–413.

Primary Examiner—Anton H. Sutto
Attorney, Agent, or Firm—Gordon F. Sieckmann; Howard C. Stanley

[57] ABSTRACT

Certain N-thiolcarbonyl derivatives of N-phosphonomethylglycinonitrile esters are novel chemical compounds having desirable herbicidal properties.

15 Claims, No Drawings

N-THIOLCARBONYL DERIVATIVES OF N-PHOSPHONOMETHYLGLYCINONITRILE ESTERS, HERBICIDAL COMPOSITIONS AND USE THEREOF

This invention relates to a new class of organic chemical compounds. More particularly, the invention is concerned with novel derivatives of esters of N-phosphonomethylglycinonitrile wherein a thiolcarbonyl group, RS(O)C—, is attached to the nitrogen atom. This class of compounds has been found to display desirable herbicidal activity when applied to certain varieties of weeds or undesired plants.

U.S. Pat. No. 3,991,095 describes the preparation of certain N-phosphonomethylglycine compounds having a thiolcarbonyl group bonded to the nitrogen atom thereof. U.S. Pat. No. 4,067,719 describes the preparation of N-phosphonomethylglycinonitriles and the herbicidal use thereof.

The compounds of the present invention are represented by the formula

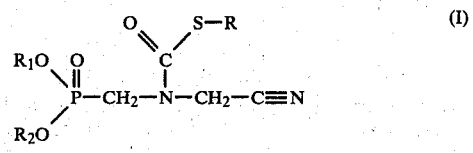

wherein R is selected from the group consisting of lower alkyl, lower cycloalkyl, lower alkenyl, phenyl, benzyl and halobenzyl and $R_1$ and $R_2$ are independently selected from the group consisting of phenyl and phenyl substituted with from one to three substituents independently selected from the class consisting of lower alkyl, lower alkoxy and halogen.

It is preferred that the substituted phenyl groups represented by $R_1$ and $R_2$ contain one or two substituents.

As employed herein, the term "lower alkyl" designates those alkyl radicals which have up to four carbon atoms in a straight or branched chain, such as, for example, methyl, ethyl, propyl, isopropyl, butyl, sec-butyl and t-butyl.

Groups illustrative of the "lower alkenyl" radicals represented by R include alkenyl radicals having from two to four carbon atoms, such as, for example, vinyl, allyl, propenyl, butenyl and the like.

Illustrative of the "lower cycloalkyl" radicals represented by R include cycloalkyl radicals containing from three to eight carbon atoms, such as, for example, cyclopropyl, cyclopentyl, cyclohexyl, cyclooctyl and the like.

By the term "halogen" as employed herein is meant chlorine, fluorine, bromine and iodine.

Illustrative of the substituted phenyl groups represented by $R_1$ and $R_2$ include mono-substituted phenyl groups wherein the substituent is in the ortho, meta or para position, such as, for example, methylphenyl, butylphenyl, methoxyphenyl, propoxyphenyl, fluorophenyl, chlorophenyl and the like and the di- and tri-substituted phenyl groups wherein the substituents are in the 2, 3, 4, 5 or 6 positions, such as, for example, diethylphenyl, dibutoxyphenyl, dichlorophenyl, propylbromophenyl, methoxyfluorophenyl, (methyl)(propoxy)phenyl and the like.

As employed herein, the term "halobenzyl" refers to benzyl groups wherein up to three hydrogens attached to the phenyl ring are replaced with halogens.

In accordance with the present invention, the compounds of formula (I) are prepared by reacting a compound of the formula

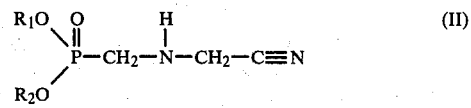

wherein $R_1$ and $R_2$ are above defined with a substituted thio chloroformate of the formula

wherein R is above defined; in the presence of a tertiary amine in an appropriate solvent within a temperature range of from about 15° C. to about 35° C.

In preparing the compounds of formula (I), the ratio of reactants can vary over a wide range. It is preferred to employ an excess of the substituted thiochloroformate of formula (III) for ease of reaction and maximum yield of product.

While the process of this invention can be conducted at atmospheric, sub-atmospheric or super-atmospheric pressure, for convenience and economy, it is generally preferred to conduct these processes at atmospheric pressure.

Solvents which may be employed in the process of this invention must cause the amine hydrochloride by-product to remain insoluble. Solvents such as benzene, ether, and the like may be employed.

The following illustrative, non-limiting examples will serve to further demonstrate to those skilled in the art the manner in which the specific compounds within the scope of this invention can be prepared. In the examples, all parts are parts by weight unless otherwise expressly stated.

EXAMPLE 1

To a mixture containing N-diphenoxyphosphinylmethylglycinonitrile (3.02 g; 0.01 mol) and triethylamine (1.01 g; 0.01 mol) in 150 ml. of benzene was added ethylthiochloroformate (0.52 g; 0.011 mol) at 26° C. The resulting reaction mixture was stirred at 26° C. for 48 hours. The reaction mixture was filtered to remove residual triethylamine hydrochloride and the filtrate was concentrated in vacuo to remove any triethylamine and then filtered through clay to yield N-ethylthiolcarbonyl-N-diphenoxyphosphinylmethylglycinonitrile hemi-hydrate (3.3 g; 84% yield) as an amber oil ($N_D^{25} = 1.5597$) having the following analysis:

Calculated: C, 54.13; H, 5.05; N, 7.01; S, 8.03. Found: C, 53.99; H, 4.99; N, 6.99; S, 8.04.

EXAMPLE 2

To a mixture containing N-diphenoxyphosphinylmethylglycinonitrile (6.00 g; 0.02 mol) and triethylamine (3.03 g; 0.03 mol) in 150 ml. of benzene was added t-butylthiochloroformate (4.6 g; 0.031 mol) at 26° C. The resulting reaction mixture was stirred at 26° C. for 48 hours. The reaction mixture was filtered to remove residual triethylamine hydrochloride and the filtrate was concentrated in vacuo to remove any triethylamine and then filtered through clay to yield N-t-butylthiolcarbonyl-N-diphenoxyphosphinylmethylglycinonitrile hemi-hydrate (6.5 g; 77% yield) as an amber oil ($N_D^{25} = 1.5444$) having the following analysis:

Calculated: C, 56.20; H, 5.66; N, 6.55. Found: C, 56.13; H, 5.68; N, 6.35.

EXAMPLE 3

To a mixture containing N-diphenoxyphosphinylmethylglycinonitrile (6.00 g; 0.02 mol) and triethylamine (2.00 g; 0.02 mol) in 150 ml. of benzene was added cyclohexylthiochloroformate (4.3 g; 0.024 mol) at 26° C. The resulting reaction mixture was stirred at 26° C. for 48 hours. The reaction mixture was filtered to remove residual triethylamine hydrochloride and the filtrate was concentrated in vacuo to remove any triethylamine and then filtered through clay to yield N-cyclohexylthiolcarbonyl-N-diphenoxyphosphinylmethylglycinonitrile (6.3 g; 71% yield) as an amber oil ($N_D^{25} - 1.5635$) having the following analysis:

Calculated: C, 59.45; H, 5.63; N, 6.30. Found: C, 59.54; H, 5.59; N, 6.59.

EXAMPLE 4

To a mixture containing N-diphenoxyphosphinylmethylglycinonitrile (12.1 g; 0.04 mol) and triethylamine (4.4 g; 0.044 mol) in 150 ml. of benzene was added allylthiochloroformate (5.6 g; 0.044 mol) at 26° C. The resulting reaction mixture was stirred at 26° C. for 48 hours. The reaction mixture was filtered to remove residual triethylamine hydrochloride and the filtrate was concentrated in vacuo to remove any triethylamine and then filtered through clay to yield N-ethylthiolcarbonyl-N-diphenoxyphosphinylmethylglycinonitrile hemi-hydrate (15.3 g; 95% yield) as an amber oil ($N_D^{25} = 1.5635$) having the following analysis:

Calculated: C, 56.71; H, 5.76; N, 7.97. Found: C, 56.50; H, 5.83; N, 7.84.

EXAMPLE 5

To a mixture containing N-diphenoxyphosphinylmethylglycinonitrile (15.1 g; 0.05 mol) and triethylamine (5.1 g; 0.05 mol) in 200 ml. of benzene was slowly added a solution of phenylthiochloroformate (10.6 g; 0.055 mol) in 50 ml. of benzene over a period of one hour. The resulting reaction mixture was stirred for 64 hours at 26° C. The reaction mixture was filtered and the residual triethylamine hydrochloride was washed with benzene. The filtrate and washings were combined and the combined solution was induced to crystallize using petroleum ether to yield a crude product. The crude product was recrystallized using petroleum ether to yield N-phenylthiolcarbonyl-N-diphenoxyphosphinylmethylglycinonitrile (4.66 g; 21% yield) as a white solid having a melting point of 86°-88° C. and the following analysis:

Calculated: C, 60.27; H, 4.37; N, 6.39; S, 7.31. Found: C, 60.10; H, 4.36; N, 6.39; S, 7.40.

EXAMPLE 6

To a mixture containing N-diphenoxyphosphinylmethylglycinonitrile (6.0 g; 0.02 mol) and triethylamine (2.0 g; 0.02 mol) in 100 ml. of benzene was added a solution of 4-chlorobenzylchloroformate (6.0 g; 0.027 mol) in 25 ml. of benzene at 26° C. The resulting reaction mixture was stirred for 46 hours and then filtered to remove residual triethylamine hydrochloride. The filtrate was concentrated in vacuo to yield an oil. Nuclear magnetic resonance analysis indicated that the reaction was not complete. The oil was dissolved in benzene and additional triethylamine and 4-chlorobenzylchloroformate added. The procedure was repeated until nuclear magnetic resonance analysis indicated that the reaction complete. The oil resulting after vacuum concentration was filtered through clay and a crude product crystallized upon standing. The crude product was recrystallized using ether to yield N-4-chlorophenylmethylthiolcarbonyl-N-diphenoxyphosphinylmethylglycinonitrile (9.3 g; 95% yield) as a white solid having a melting point of 73°-74° C. and the following analysis:

Calculated: C, 56.74; H, 4.14; N, 5.75. Found: C, 56.96; H, 4.11; N, 5.32.

EXAMPLE 7

Following the procedure of Example 5, isopropylthiochloroformate (1.52 g; 0.011 mol) was reacted with N-diphenoxyphosphinylmethylglycinonitrile (3.02 g; 0.01 mol) to yield N-isopropylthiolcarbonyl-N-diphenoxyphosphinylmethylglycinonitrile (3.65 g; 90% yield) as an amber oil, $n_D^{25} = 1.5530$ and having the following analysis:

Calculated: C, 56.43; H, 5.23; N, 6.93. Found: C, 56.60; H, 5.31; N, 7.36.

EXAMPLE 8

To a slurry containing N-bis(3-methyl-4-chlorophenoxy)phosphinylmethylglycinonitrile methane sulfonic acid salt (10 g; 0.02 mol) and triethylamine (2.0 g; 0.02 mol) in 100 ml. of benzene was added 4-chlorobenzylthiochloroformate (4.6 g; 0.021 mol). The reaction mixture was stirred for 64 hours, then filtered to remove residual triethylaminehydrochloride. The filtrate was washed twice with water, dried over magnesium sulfate and then concentrated in vacuo to yield a dark amber oil. The amber oil was crystallized from ether-cyclohexane to yield a crude product which was recrystallized from methanol-ether-petroleum ether to yield N-(4-chlorophenylmethylthiol)carbonyl-N-bis(3-methyl-4-chlorophenoxy)phosphinylmethylglycinonitrile (1.8 g; 15% yield) as a white solid having a melting point of 70°-73° C. and the following analysis:

Calculated: C, 51.43; H, 3.80; N, 4.80; Cl, 18.22. Found: C, 51.62; H, 3.81; N, 4.88; Cl, 18.20.

EXAMPLE 9

Ethylthiochloroformate (2.6 g; 0.20 mol) was added to the solution formed by a slurry of di(4-methoxyphenoxy)phosphinylmethylglycinonitrile methane sulfonic acid salt (9.2 g; 0.02 mol) and triethylamine (2.2 g; 0.22 mol) in benzene (100 ml.). After a short time, triethylamine hydrochloride began to precipitate. The resulting slurry was stirred for about 64 hours. The slurry was filtered to remove the triethylamine hydrochloride. The filtrate was concentrated. The resulting residue was dissolved in methylene chloride and washed with water. The methylene chloride layer was dried and then concentrated to yield N-ethylthiolcarbonyl-N-di(4-methoxyphenoxy)phosphinylmethylglycinonitrile (5.0 g; 55% yield) as a light yellow oil, $n_D^{27} = 1.5614$ and having the following analysis:

Calculated: C, 53.33; H, 5.11; N, 6.33. Found: C, 53.11; H, 5.22; N, 6.75.

EXAMPLE 10

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical. In that 6 ml. is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Tables I and II is as follows:

| Plant Response | Index |
| --- | --- |
| 0 –24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
| --- | --- |
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

TABLE I

| Compound of Example No. | WAT | kg/h | A | B | C | D | E | F | G | H | I | J | K |
| --- | --- | --- | --- | --- | --- | --- | --- | --- | --- | --- | --- | --- | --- |
| 1 | 4 | 11.2 | 2 | 2 | 1 | 1 | 2 | 2 | 1 | 2 | 3 | 1 | 2 |
| 1 | 4 | 5.6 | 1 | 1 | 1 | — | 1 | 1 | 1 | 0 | 3 | 0 | 1 |
| 2 | 4 | 11.2 | 1 | 2 | 1 | 2 | 2 | 3 | 2 | 0 | 0 | 0 | 2 |
| 2 | 4 | 5.6 | 1 | 1 | 0 | 1 | 0 | 1 | 1 | 0 | 0 | 0 | 1 |
| 3 | 4 | 11.2 | 1 | 2 | 0 | 2 | 0 | 1 | 2 | 0 | 3 | 0 | 2 |
| 3 | 4 | 5.6 | — | 1 | 0 | 1 | 1 | 0 | — | 2 | 0 | 1 | |
| 4 | 4 | 11.2 | 1 | 2 | 1 | 2 | 3 | 4 | 2 | 1 | 1 | 1 | 3 |
| 4 | 4 | 5.6 | 2 | 2 | 0 | 1 | 1 | 3 | 1 | 0 | 1 | 0 | 3 |
| 5 | 4 | 11.2 | 2 | 2 | 0 | 2 | 1 | 1 | 2 | 0 | 1 | 0 | 3 |
| 5 | 2 | 5.6 | 0 | 1 | 0 | 1 | 1 | 0 | 0 | 1 | 0 | 0 | 0 |
| 6 | 4 | 11.2 | 1 | 2 | 1 | 2 | 2 | 3 | 1 | 0 | 0 | 0 | 2 |
| 6 | 2 | 5.6 | 0 | 0 | 0 | 0 | 0 | 0 | 0 | 0 | 0 | 0 | 0 |
| 7 | 4 | 11.2 | 2 | 4 | 3 | 3 | 2 | 4 | 2 | 1 | 3 | 2 | 4 |
| 7 | 4 | 5.6 | 1 | 2 | 1 | — | 1 | 4 | 2 | 0 | 3 | 1 | 3 |
| 8 | 2 | 11.2 | 0 | 0 | 0 | 0 | 1 | 0 | 0 | 0 | 0 | 0 | 0 |
| 8 | 2 | 5.6 | 0 | 0 | 0 | 0 | 0 | 0 | 0 | 0 | 0 | 0 | 0 |
| 9 | 4 | 11.2 | 0 | 1 | 0 | 1 | 2 | 0 | 1 | 0 | 0 | 0 | 1 |
| 9 | 4 | 5.6 | 0 | 1 | 0 | 1 | 1 | 0 | 0 | 0 | 0 | 0 | 0 |

TABLE II

| Compound of Example No. | WAT | kg/h | L | M | N | O | P | B | Q | D | R | E | F | C | J | S | K | T |
| --- | --- | --- | --- | --- | --- | --- | --- | --- | --- | --- | --- | --- | --- | --- | --- | --- | --- | --- |
| 2 | 4 | 5.6 | 0 | 0 | 0 | 1 | 2 | — | 2 | 2 | 4 | 2 | 2 | 1 | 1 | 1 | 3 | 3 |
| 2 | 2 | 1.12 | 0 | 0 | 0 | 0 | 0 | 0 | 1 | 1 | — | 0 | 0 | 0 | 0 | 0 | 0 | 2 |
| 3 | 4 | 5.6 | 0 | 0 | 0 | 1 | 2 | — | 0 | 2 | 4 | 2 | 1 | 1 | 0 | 1 | 2 | 3 |
| 3 | 2 | 1.12 | 0 | 0 | 0 | 0 | 0 | — | 0 | 0 | 3 | 1 | — | 0 | 0 | 0 | 0 | 1 |
| 3 | 2 | 0.28 | 0 | 0 | 0 | 0 | 0 | 0 | 0 | 0 | 0 | 0 | 0 | 0 | 0 | 0 | 0 | 0 |
| 4 | 4 | 5.6 | 1 | 1 | 1 | 2 | 2 | 2 | 2 | 2 | — | 4 | 4 | 1 | 1 | 2 | 2 | 3 |
| 4 | 2 | 1.12 | 0 | 0 | 0 | 0 | 0 | 0 | 1 | 1 | — | — | 1 | 0 | 0 | 0 | 2 | 1 |
| 4 | 2 | 0.28 | 0 | 0 | 0 | 0 | 0 | 0 | 0 | 0 | — | 1 | 1 | 0 | 0 | 0 | 0 | 1 |
| 5 | 4 | 5.6 | 1 | 1 | 0 | 0 | 1 | 1 | 3 | 2 | — | 4 | 0 | 1 | 0 | 2 | 1 | 4 |
| 5 | 4 | 1.12 | 0 | 0 | 0 | 0 | 0 | 0 | 0 | 0 | 0 | 2 | 0 | 0 | 0 | 0 | 0 | 2 |
| 6 | 2 | 5.6 | 1 | 0 | 0 | 0 | 0 | 0 | 0 | 1 | — | 1 | 0 | 0 | 0 | 0 | 1 | 2 |
| 6 | 2 | 1.12 | 0 | 0 | 0 | 0 | 0 | 0 | 0 | 0 | 0 | 0 | 0 | 0 | 0 | 0 | 0 | 0 |
| 7 | 4 | 5.6 | 0 | 0 | 1 | 0 | 2 | — | 0 | 1 | 0 | 2 | 1 | 1 | 2 | 2 | 1 | 2 |
| 7 | 4 | 1.12 | 0 | 0 | 0 | 0 | 0 | 0 | 0 | 1 | 0 | 1 | 0 | 0 | 0 | 0 | 0 | 2 |

TABLE II-continued

| Compound of Example No. | WAT | kg/h | L | M | N | O | P | B | Q | D | R | E | F | C | J | S | K | T |
|---|---|---|---|---|---|---|---|---|---|---|---|---|---|---|---|---|---|---|
| 7 | 2 | 0.28 | 0 | 0 | 0 | 0 | 0 | 0 | — | 0 | — | 0 | 0 | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

The following list gives some specific herbicidal compositions of this invention. It is to be realized that the solvents and surfactants are interchangeable in the composition.

| | | |
|---|---|---|
| 1. | N-ethylthiolcarbonyl-N-diphenoxyphosphinylmethylglycinonitrile hemi-hydrate | 95 parts |
| | Methanol | 5 parts |
| 2. | N-t-butylthiolcarbonyl-N-diphenoxyphosphinylmethylglycinonitrile hemi-hydrate | 95 parts |
| | Ethoxylated nonyl phenol | 5 parts |
| 3. | N-cyclohexylthiolcarbonyl-N-diphenoxyphosphinylmethylglycinontrile | 90 parts |
| | Isopropanol | 10 parts |
| 4. | N-ethylthiolcarbonyl-N-diphenoxyphosphinylmethylglycinonitrile hemi-hydrate | 90 parts |
| | Ethoxylated octyl phenol | 10 parts |
| 5. | N-phenylthiolcarbonyl-N-diphenoxyphosphinylmethylglycinonitrile | 90 parts |
| | Chloroform | 5 parts |
| | Ethoxylated dinonyl phenol | 5 parts |
| 6. | N-4-chlorophenylmethylthiolcarbonyl-N-diphenoxyphosphinylmethylglycinonitrile | 75 parts |
| | Butanol | 25 parts |
| 7. | N-isopropylthiolcarbonyl-N-diphenoxyphosphinylmethylglycinonitrile | 75 parts |
| | Ethoxylated oleyl alcohol | 25 parts |
| 8. | N-(4-chlorophenylmethylthiol)-carbonyl-N-bis(3-methyl-4-chlorophenoxy)phosphinylmethylglycinonitrile | 75 parts |
| | Acetonitrile | 15 parts |
| | Ethoxylated cocoamine | 10 parts |
| 9. | N-ethylthiolcarbonyl-N-di(4-methoxyphenoxy)phosphinylmethylglycinonitrile | 75 parts |
| | 1,2-Dimethoxyethane | 20 parts |
| | Ethoxylated tallow amine | 5 parts |
| 10. | N-ethylthiolcarbonyl-N-diphenoxyphosphinylmethylglycinonitrile hemi-hydrate | 50 parts |
| | Dimethylformamide | 50 parts |
| 11. | N-t-butylthiolcarbonyl-N-diphenoxyphosphinylmethylglycinonitrile heni-hydrate | 50 parts |
| | Isopropyl dodecylbenzene sulfonate | 50 parts |
| 12. | N-cyclohexylthiolcarbonyl-N-diphenoxyphosphinylmethylglycinonitrile | 50 parts |
| | Dimethylsulfoxide | 40 parts |
| | Ethoxylated soybeanamine | 10 parts |
| 13. | N-ethylthiolcarbonyl-N-diphenoxyphosphinylmethylglycinonitrile hemi-hydrate | 50 parts |
| | γ-butyrolactone | 25 parts |
| | Triethanolamine dodecylbenzene sulfonate | 25 parts |
| 14. | N-phenylthiolcarbonyl-N-diphenoxyphosphinylmethylglycinonitrile | 50 Parts |
| | 1,1,1-Trichloroethane | 42 parts |
| | Ethoxylated nonyl phenol | 8 parts |
| 15. | N-4-chlorophenylmethylthiolcarbonyl-N-diphenoxyphosphinylmethylglycinonitrile | 25 parts |
| | Chloroform | 75 parts |
| 16. | N-isopropylthiolcarbonyl-N-diphenoxyphosphinylmethylgly- | 25 parts |

| | -continued | |
|---|---|---|
| | cinonitrile | |
| | Chloroform | 70 parts |
| | Ethoxylated tallow amine | 5 parts |
| 17. | N-(4-chlorophenylmethylthiol)-carbonyl-N-bis(3-methyl-4-chlorophenoxy)phosphinylmethyl-glycinonitrile | 25 parts |
| | 1,1,1-Trichloroethane | 74 parts |
| | Ethoxylated oleyl alcohol | 1 part |
| 18. | N-ethylthiolcarbonyl-N-di(4-methoxyphenoxy)phosphinylmethyl-glycinonitrile | 25 parts |
| | Chloroform | 68 parts |
| | Ethoxylated dinonyl phenol | 7 parts |
| 19. | N-ethylthiolcarbonyl-N-diphenoxyphosphinylmethylgly-cinonitrile hemi-hydrate | 10 parts |
| | Chloroform | 90 parts |
| 20. | N-t-butylthiolcarbonyl-N-diphenoxyphosphinylmethylgly-cinonitrile hemi-hydrate | 10 parts |
| | Methanol | 80 parts |
| | Polyoxypropylene - polyoxy-ethylene block copolymer | 10 parts |
| 21. | N-cyclohexylthiolcarbonyl-N-diphenoxyphosphinylmethylgly-cinonitrile | 10 parts |
| | Ethanol | 88 parts |
| | Polyoxyethylene (20) sorbitan-monolaurate | 2 parts |
| 22. | N-ethylthiolcarbonyl-N-diphenoxyphosphinylmethylgly-cinonitrile hemi-hydrate | 10 parts |
| | Isopropanol | 72 parts |
| | Polyoxyethylene sorbitan-monooleate | |
| 23. | N-phenylthiolcarbonyl-N-diphenoxyphosphinylmethylgly-cinonitrile | 5 parts |
| | Dimethylformamide | 95 parts |
| 24. | N-4-chlorophenylmethylthiol-carbonyl-N-diphenoxyphos-phinylmethylglycinonitrile | 5 parts |
| | Acetonitrile | 90 parts |
| | Ethoxylated tallow amine | 5 parts |
| 25. | N-isopropylthiolcarbonyl-N-diphenoxyphosphinylmethylgly-cinonitrile | 5 parts |
| | Ethanol | 94 parts |
| | Ethoxylated tallow amine | 1 part |
| 26. | N-(4-chlorophenylmethylthiol)-carbonyl-N-bis(3-methyl-4-chlorophenoxy)phosphinylmethyl-glycinonitrile | 5 parts |
| | Isopropanol | 80 parts |
| | Ethoxylated cocoamine | 15 parts |

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises contacting said plants or the plant growth medium with a herbicidal amount of a compound of the formula

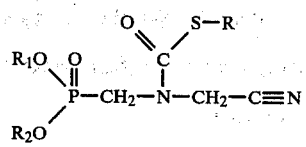

wherein R is selected from the group consisting of lower alkyl, lower cycloalkyl, lower alkenyl, phenyl, benzyl and halobenzyl and $R_1$ and $R_2$ are independently selected from the group consisting of phenyl and substituted phenyl containing from one to three substituents independently selected from the class consisting of lower alkyl, lower alkoxy and halogen.

2. A method according to claim 1 wherein $R_1$ and $R_2$ are independently selected from the group consisting of phenyl and substituted phenyl containing one or two substituents independently selected from the class consisting of lower alkyl, lower alkoxy and halogen.

3. A method according to claim 2 wherein R is lower alkyl or lower alkenyl.

4. A method according to claim 3 wherein the compound is N-t-butylthiolcarbonyl-N-diphenoxyphosphinylmethylglycinonitrile.

5. A method according to claim 4 wherein the compound is N-(2-propenylthiolcarbonyl)-N-diphenoxyphosphinylmethylglycinonitrile.

6. A compound of the formula

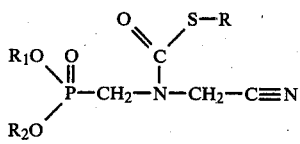

wherein R is selected from the group consisting of lower alkyl, lower cycloalkyl, lower alkenyl, phenyl, benzyl and halobenzyl and $R_1$ and $R_2$ are independently selected from the group consisting of phenyl and substituted phenyl containing from one to three substituents independently selected from the class consisting of lower alkyl, lower alkoxy and halogen.

7. A compound according to claim 6 wherein $R_1$ and $R_2$ are independently selected from the group consisting of phenyl and substituted phenyl containing one or two substituents independently selected from the class consisting of lower alkyl, lower alkoxy and halogen.

8. A compound according to claim 7 wherein R is lower alkyl or lower alkenyl.

9. A compound according to claim 8 wherein the compound is N-t-butylthiolcarbonyl-N-diphenoxyphosphinylmethylglycinonitrile.

10. A compound according to claim 9 wherein the compound is N-(2-propenylthiolcarbonyl)-N-diphenoxyphosphinylmethylglycinonitrile.

11. A herbicidal composition comprising an inert adjuvant and a herbicidally effective amount of a compound of the formula

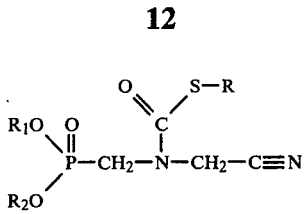

wherein R is selected from the group consisting of lower alkyl, lower cycloalkyl, lower alkenyl, phenyl, benzyl and halobenzyl and $R_1$ and $R_2$ are independently selected from the group consisting of phenyl and substituted phenyl containing from one to three substituents independently selected from the class consisting of lower alkyl, lower alkoxy and halogen.

12. A composition according to claim 11 wherein $R_1$ and $R_2$ are independently selected from the group consisting of phenyl and substituted phenyl containing one or two substituents independently selected from the class consisting of lower alkyl, lower alkoxy and halogen.

13. A composition according to claim 12 wherein R is lower alkyl or lower alkenyl.

14. A composition according to claim 13 wherein the compound is N-t-butylthiolcarbonyl-N-diphenoxyphosphinylmethylglycinonitrile.

15. A composition according to claim 14 wherein the compound is N-(2-propenylthiolcarbonyl)-N-diphenoxyphosphinylmethylglycinonitrile.

* * * * *